(12) United States Patent
Wagner

(10) Patent No.: US 7,070,413 B1
(45) Date of Patent: Jul. 4, 2006

(54) ORAL APPLICATOR

(76) Inventor: Eugene C. Wagner, 1626 Chastain Pkwy East, Pacific Palisades, CA (US) 90272

( * ) Notice: Subject to any disclaimer, the term of this patent is extended or adjusted under 35 U.S.C. 154(b) by 0 days.

(21) Appl. No.: 11/238,392

(22) Filed: Sep. 30, 2005

Related U.S. Application Data

(63) Continuation-in-part of application No. 10/998,705, filed on Nov. 29, 2004, which is a continuation-in-part of application No. 10/423,664, filed on Apr. 25, 2003, now Pat. No. 6,840,771.

(51) Int. Cl.
*A61C 15/00* (2006.01)

(52) U.S. Cl. ........................................ 433/214; 433/216

(58) Field of Classification Search .................... 433/6, 433/80, 71, 214, 215, 216; 604/77
See application file for complete search history.

(56) References Cited

U.S. PATENT DOCUMENTS

| | | | |
|---|---|---|---|
| 516,529 A | | 3/1894 | Hansen |
| 2,171,695 A | | 9/1939 | Harper |
| 2,933,811 A | | 4/1960 | Lifton |
| 3,064,354 A | * | 11/1962 | Pos .............................. 433/71 |
| 3,527,219 A | | 9/1970 | Greenberg |
| 3,567,823 A | | 3/1971 | Yamaga |
| 3,577,640 A | | 5/1971 | Lee |
| 3,624,909 A | | 12/1971 | Greenberg |
| 3,688,406 A | * | 9/1972 | Porter et al. .............. 433/217.1 |
| 4,173,219 A | | 11/1979 | Lentine |
| 4,776,792 A | | 10/1988 | Wagner |
| 4,867,680 A | | 9/1989 | Hare |
| 5,165,424 A | | 11/1992 | Silverman |
| 5,302,374 A | | 4/1994 | Wagner |
| 5,562,449 A | | 10/1996 | Jacobs |
| 5,566,684 A | | 10/1996 | Wagner |
| 5,575,654 A | | 11/1996 | Fontenot |
| 5,611,687 A | | 3/1997 | Wagner |
| 5,863,202 A | | 1/1999 | Fontenot |
| 5,891,453 A | | 4/1999 | Sagel |
| 5,957,689 A | * | 9/1999 | Wagner ....................... 433/215 |
| 5,989,569 A | | 11/1999 | Dirksing |
| 6,096,328 A | | 8/2000 | Sagel |
| 6,126,443 A | | 10/2000 | Burgio |
| 6,274,122 B1 | | 8/2001 | McLaughlin |
| 6,364,665 B1 | | 4/2002 | Trettenero |
| 6,379,147 B1 | | 4/2002 | Georgakis |
| 6,422,868 B1 | | 7/2002 | Lindquist |
| 6,506,053 B1 | | 1/2003 | Wiesel |
| 6,514,484 B1 | | 2/2003 | Rajaiah |
| 6,517,350 B1 | | 2/2003 | Diasti |
| 6,860,736 B1 | * | 3/2005 | Allred et al. ................. 433/80 |

(Continued)

*Primary Examiner*—Todd E. Manahan
(74) *Attorney, Agent, or Firm*—Seth Natter; Natter & Natter

(57) ABSTRACT

An applicator for oral treatment preparations comprises a membrane covered core having an arched vertical panel and a lateral panel with a generally "L" shaped transverse cross section. The core is formed of a modeling material such as wax, which is soft and pliable and which conforms to the contours of oral surfaces against which it manipulated. The vertical panel is pressed against buccal dentition surfaces to be treated. The lateral panel is then manually bent around occlusal surfaces and pressed against lingual dentition surfaces. The oral treatment preparation for administration may be coated on the membrane prior to fitting or microencapsulated within the core to pass through the membrane for administration. Alternately the applicator is removed after initial shaping or fitting, the oral treatment preparation is applied to the membrane and the applicator is then reinserted.

19 Claims, 2 Drawing Sheets

U.S. PATENT DOCUMENTS

| | | |
|---|---|---|
| 6,896,518 B1 * | 5/2005 | Jacobs et al. ............... 433/215 |
| 6,948,936 B1 * | 9/2005 | Miller et al. ................ 433/214 |
| 2001/0044096 A1 | 11/2001 | Lindquist |
| 2002/0081555 A1 * | 6/2002 | Wiesel ....................... 433/215 |
| 2002/0146666 A1 | 10/2002 | Sagel |
| 2003/0003421 A1 * | 1/2003 | Bestenheider et al. ...... 433/215 |
| 2004/0110111 A1 | 6/2004 | Wasylucha |
| 2004/0131561 A1 | 7/2004 | McLaughlin |

* cited by examiner

ORAL APPLICATOR

RELATED APPLICATIONS

This application is a continuation-in-part of application Ser. No. 10/998,705, filed Nov. 29, 2004, which is a continuation-in-part of application Ser. No. 10/423,664, filed Apr. 25, 2003, now U.S. Pat. No. 6,840,771 issued Jan. 11, 2005.

BACKGROUND OF THE INVENTION

1. Field of the Invention

This invention relates generally to applicators for topically applied oral preparations and more particularly to an applicator having a membrane covered pliable modeling core for efficacious delivery of an oral treatment preparation.

2. Antecedents of the Invention

Significant advances in the administration of topical oral preparations have evolved in recent years. For example, tooth whitening is no longer relegated to the costly and time consuming procedures rendered by the dental practitioner. Various approaches have evolved for practicing tooth whitening procedures without participation of the dental practitioner.

Among the early tooth whitening systems for do-it-yourself usage was a paste or gel containing a hydrogen peroxide or carbamide peroxide constituent. The gel or paste was applied to tooth surfaces by, for example, a toothbrush, a cotton swab, etc.

Unfortunately, such systems failed to provide readily noticeable results, due to a combination of factors including the limited time duration of application as well as the dilution of effective whitening or bleaching constituent within the oral cavity by saliva. Further, gingival surfaces were engaged by the whitening or bleaching constituent, leading to possible gingival initiation or other undesired effects.

Improved tooth whitening procedures included the admixture of conventional toothpaste together with a tooth whitening preparation, as described in U.S. Pat. No. 5,302,374 issued Apr. 12, 1994 and U.S. Pat. No. 5,597,554 issued Jan. 28, 1997 to applicant herein. The employment of such technique resulted in decreased tooth surface wear as well as an increase in the rate of efficacious release of the whitening or bleaching constituent of the tooth whitening preparation.

A further approach at providing an effective delivery system for a topical oral treatment preparation included the system disclosed in U.S. Pat. No. 5,611,687 which issued Mar. 18, 1997 to applicant herein. Such system comprised and applicator for carrying and applying a liquid preparation solely upon buccal surfaces of target teeth. The liquid preparation was drawn to an applicator tip by capillary action. To administer a coating of tooth whitening preparation on selected tooth enamel surfaces, the tip was wiped over the surfaces to be treated.

Other attempts at improving the self administration of oral treatment preparations included utilizing a fitted dental trough which surrounded buccal, occlusal and lingual tooth surfaces, as disclosed in U.S. Pat. No. 5,165,424 issued Nov. 24, 1992. The system disclosed therein did not attain widespread commercial success, perhaps due to the fact that the device was ungainly and impeded speech. It could not, therefore, be worn in any environment wherein social encounters might be anticipated. Further, the device did not assure controlled administration of the oral treatment preparation on only selected tooth surfaces.

A further self administration approach comprised the utilization of flexible strips preloaded with a tooth whitening preparation, as disclosed in U.S. Pat. No. 5,891,453 issued Apr. 6, 1999. The flexible strips disclosed therein were unable to attain a true impression of the user's buccal dentition; it could not intimately enter interdental crevices, for example. Further, the user was not able to control the concentration of tooth whitening preparation or limit the application to selected target teeth or tooth surfaces. A further disadvantage was that the tooth whitening preparation was often in contact with gingival surfaces, which often led to gingival irritation.

There remained a need to provide an efficient applicator for controlled topical administration of preparations suitable for oral applications, such as, tooth whitening, oral hygiene, prophylaxis, desentization, palliation, etc.

SUMMARY OF THE INVENTION

An oral applicator includes a soft putty like pliable core of formative material capable of receiving a dental impression by manual manipulation. A plastic film stratum membrane covers the core. The applicator is configured as a dental arch and may include a curved vertical panel and a lateral panel.

The applicator is custom fitted by impressing the contours of target oral surfaces into the applicator through manual manipulation of the pliable core. Modeling of buccal surfaces into the core may be facilitated with an arched backing plate and exerting lateral force against the backing plate.

Impressions of buccal surfaces of target teeth to be treated are thus modeled in an inner face of the vertical panel, with the film membrane serving to maintain dimensional integrity and stability of the applicator in reduced thickness areas of the core.

The lateral panel of the applicator is then deformed by manipulation over occlusal surfaces and against lingual surfaces and pressure is applied in labial and buccal directions to model the remaining dentition surfaces into the pliable core.

The applicator may then be removed and an oral treatment preparation is deposited on selected contoured surfaces of the membrane, corresponding to the surfaces to be treated. Alternatively or conjunctively, the oral treatment preparation is applied to the target oral surfaces. Thereafter, the applicator is repositioned to provide intimate undiluted engagement between the treatment preparation and the surfaces to be treated.

Optionally, the applicator may be preloaded with an oral treatment preparation coated on contact faces of the core or carried in wells, pockets or microcapsules and the membrane may include perforations or is otherwise permeable, such that the oral treatment preparation is dispensed through the membrane. Alternately, the oral treatment preparation may be impregnated in the membrane or perforations thereof.

The core may also be fabricated as a single membrane covered sheet which is bent into an arched trough having a "U" or "V" shaped transverse section. The trough is inserted into the oral cavity to overly the surfaces to be treated and to be deformed to model the buccal, lingual and occlusal dentition contours.

Separate applicators are fitted for the maxillary dentition and the mandibular dentition for simultaneous treatment of target surfaces in both, or the maxillary and mandibular dentitions may be treated individually.

From the foregoing compendium, it will be appreciated that it is an aspect of the present invention to provide an oral applicator having a pliable core of the general character described which is not subject to the disadvantages of the antecedents of the invention aforementioned.

It is a feature of the present invention to provide an oral applicator having a pliable core of the general character described with a simplified procedure for custom fitting.

A consideration of the present invention is to provide an oral applicator having a pliable core of the general character described which precludes undesirable surface exposure of oral treatment preparations to surfaces other than target surfaces.

A further aspect of the present invention is to provide an oral applicator having a pliable core of the general character described which assures against dilution of an oral treatment preparation.

To provide an oral applicator having a pliable core of the general character described which does not impede speech during usage is a further consideration of the present invention.

Another feature of the present invention is to provide an oral applicator having a pliable core of the general character described which is low in cost and suitable for manufacture by economical mass production fabrication.

To provide an oral applicator having a pliable core of the general character described which permits the user to control the dosage of an oral treatment preparation administered to selected tooth surfaces is a further aspect of the present invention.

Another feature of the present invention is to provide an oral applicator having a pliable core of the general character described which is compatible with the administration of any of a number of available treatment preparations.

A still further aspect of the present invention is to provide an oral applicator having a pliable core of the general character described which is both safe and efficacious.

Yet another feature of the present invention is to provide an oral applicator having a pliable core of the general character described which does not inhibit a user's social activities during administration of an oral treatment preparation.

Other aspects, features and considerations of the present invention in part will be obvious and in part will be pointed out hereinafter.

With these ends in view, the invention finds embodiment in the various combinations of elements, arrangements of parts and series of steps by which the said aspects, features and considerations aforementioned and certain other aspects, features and considerations are attained, all with reference to the following description and drawings and the scope of which will be more particularly pointed out and indicated in the appended claims.

BRIEF DESCRIPTION OF THE DRAWINGS

It should be noted that in the drawings, which are to briefly described hereinafter, for clarity of illustration and understanding, elements of the figures have not necessarily been drawn to scale and certain elements have been omitted in some of the figures. For example, the dimensions of some of the elements may be exaggerated relative to the other elements.

In the accompanying drawings, in which are shown some of the various exemplary embodiments of the invention.

DESCRIPTION OF THE PREFERRED EMBODIMENTS

Figure 1:
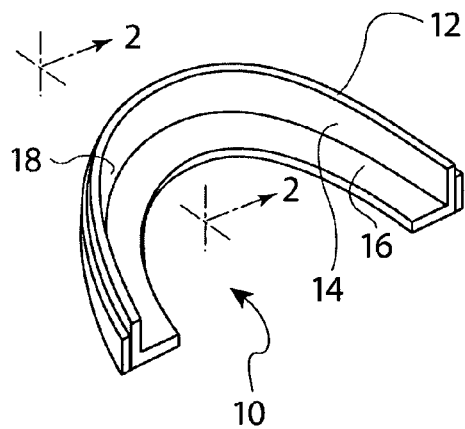
FIG. 1 is a perspective illustration of an oral applicator constructed in accordance with and embodying the invention prior to custom fitting and showing a soft pliable core covered with a plastic film membrane, and with a backing plate employed to facilitate modeling impressions of oral surfaces to be treated.
Figure 2:
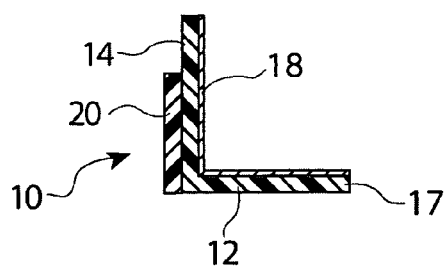
FIG. 2 is an enlarged scale sectional view through the applicator, the same taken substantially about the plane 2—2 of FIG. 1 and showing vertical and lateral panels of the core.

Incorporated herein by reference U.S. Pat. No. 6,840,771.

Referring now in detail to the drawings, the reference numeral 10 denotes generally an oral applicator constructed in accordance with and embodying the invention. The applicator 10 provides efficacious administration of a topical oral treatment preparation on selected oral surfaces.

Pursuant to the invention, the applicator 10 includes a pliable core 12 formed of modeling material, i.e. material suitable for employment in modeling dental impressions by manual manipulation, as opposed to molding by cooling or curing a flowable material.

Preferably, the core 12 is clear or white and the modeling material comprises a nonreactive, inert material which is soft and pliable at or below body temperature. Suitable materials having such characteristics include various waxes employed in the dental field or blends of waxes. Among the suitable dental waxes are utility waxes available from Sullivan-Schein Dental of Melville, N.Y., including Henry Schein® utility wax strips and Heraeus Kulzer utility wax strips, soft orthodontic wax available from Kerr Corporation of Orange, Calif. and waxes available from Kindt-Collins of Cleveland Ohio.

Other modeling materials having rheological characteristics suitable for implementation as the core 12 include nonreactive inert plastic putty, modeling clay, etc., which are deformable under manual manipulation at temperatures below those which would cause discomfort within the oral cavity.

The core 12 may be dimensioned as a strip initially having uniform thickness in the range of approximately ½ mm to 3 mm. The core 12 may have the configuration of an arched vertical panel 14 having a height of approximately 10 mm to 15 mm and a planar lateral panel 16, having a length in the range of 12 mm to 18 mm. The lateral panel 16 is substantially perpendicular to the vertical panel 14, so that the core 12 is "L" shaped in transverse cross section.

Figure 7:
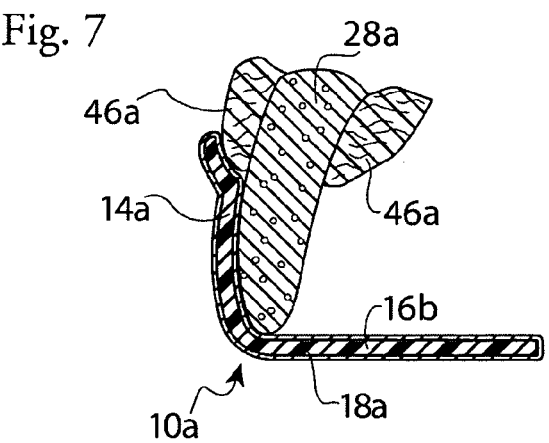
FIG. 7 is a sectional view, similar to FIG. 4, illustrating a modified applicator with a film membrane completely encasing the core.
Figure 8:
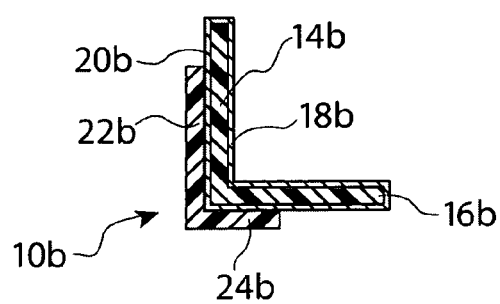
FIG. 8 is an enlarged scale sectional view, similar to FIG. 2, of a modified applicator and modified backing plate which includes an occlusal ledge which supports the lateral panel of the core with the core being encased in a plastic film membrane.
Figure 9:
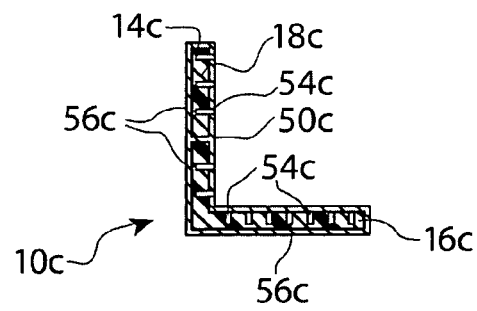
FIG. 9 is an enlarged scale sectional view, similar to the views of FIGS. 2 and 8, through a further embodiment of the invention, wherein an applicator is preloaded with tooth whitening preparation and a membrane includes perforations.

Pursuant to the invention, at least one face of the panels 14, 16 is overlaid with a thin plastic film stratum membrane 18. For the sake of clarity, the membrane 18 is not illustrated in FIG. 1, FIG. 3 and FIG. 5 which are of reduced scale. As shown in FIGS. 7–9, the entire core may be covered, encased or overlaid by a thin plastic film stratum membrane.

The membrane 18 may be comprised of a clear self-adherent plastic film such as those commonly employed as food grade plastic wrap, including, but not limited to, plastic films formed of low density polyethylene, polyvinyl chloride and polyvinylidene chloride and may be permeable or include perforations to facilitate dispensing an oral treatment preparation.

Figure 5:
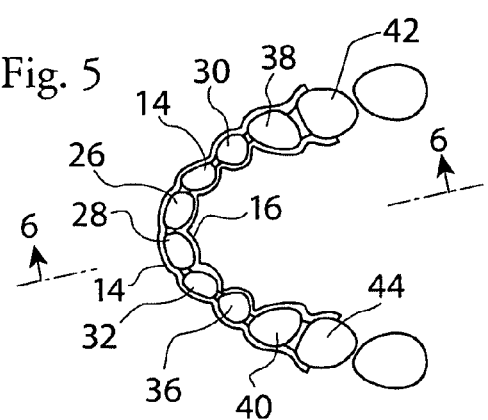
FIG. 5 is a bottom plan view, similar to FIG. 3, however showing a completely fitted applicator with the backing plate removed and the lateral panel modeled around lingual dentition contours.

The contours of buccal tooth and gingival surfaces are impressed into the vertical panel 14 of the applicator 10 by registering the applicator 10 against such surfaces and applying lateral compressive forces. One may employ digital pressure for the application of such forces directly against the panel 14, resulting in contoured deformation of the outer surface of the panel, as illustrated in FIG. 5, or may exert such forces against a curved backing plate 20 which abuts an outer face of the vertical panel 14.

As illustrated in FIG. 1, the backing plate 20 is shaped as an arcuate semi-cylindrical panel 22. The backing plate 20 may be formed of a thermoplastic resin, such as those disclosed in U.S. Pat. No. 6,840,771. Employment of the backing plate 20 is optional.

Figure 3:
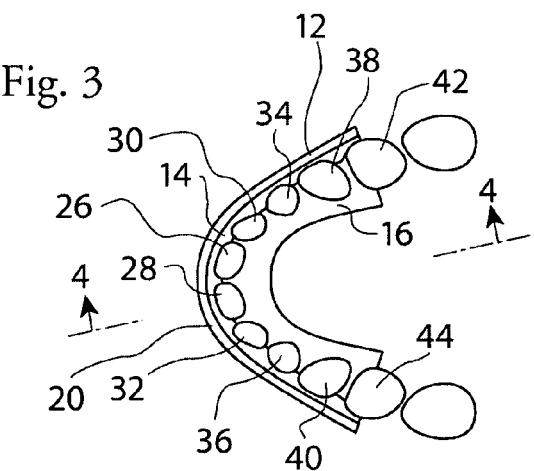
FIG. 3 is a bottom plan view of the applicator during an initial fitting stage, and showing the vertical panel modeled around the buccal and interdental contours of selected target teeth of a maxillary dentition prior to bending the lateral panel.

As heretofore mentioned, the applicator 10 is constructed to facilitate administration of an oral treatment preparation only upon dentition surfaces in need of treatment. With reference to FIG. 3 comprising a bottom view of a maxillary dentition arch, it should be noted that the arch is symmetrically arrayed and includes at least a pair of central incisors 26, 28, a pair of lateral incisors 30, 32, a pair of cuspids 34, 36, a pair of first bicuspids 38, 40 and a pair of second bicuspids 42, 44.

The applicator 10 is dimensionally configured, by way of example only, for administering an oral treatment preparation to selected surfaces of any or all of the following teeth and, if desired, adjacent gingival tissue: the central incisors 26, 28, the lateral incisors, 30, 32 the cuspids 34, 36 and the first bicuspids 38,40. A differently dimensioned applicator may be employed should one wish to treat the second bicuspids 42, 44 and/or molars. It is also within the purview of the invention to provide an applicator 10 dimensioned only to accommodate a segmental portion of a dentition, e.g. only the lateral incisor 32 and adjacent cuspid 36.

The applicator 10 is provided in predetermined sizes; it may be filmished in varying lengths such as to accommodate selected target surfaces in need of treatment or may be provided of an extended length, with the user trimming either or both ends, such that the trimmed applicator will accommodate the target surfaces.

Figure 4:
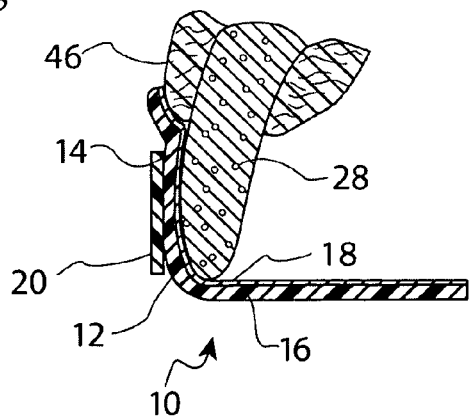
FIG. 4 is an enlarged scale sectional view through the applicator, the same being taken substantially along the plane 4—4 of FIG. 3 and showing the inner face of the applicator core modeled with the impression of the buccal surface of a user's central incisor and adjacent gingival tissue.

With reference now to FIGS. 3–4, it will be seen that portions of an inner face of the vertical panel 14, are forced around buccal tooth surfaces, between interdental tooth surfaces and also around gingival tissue 46. If the backing plate 20 was employed, it is stripped from the vertical panel 14 after the vertical panel has been so modeled.

Figure 6:
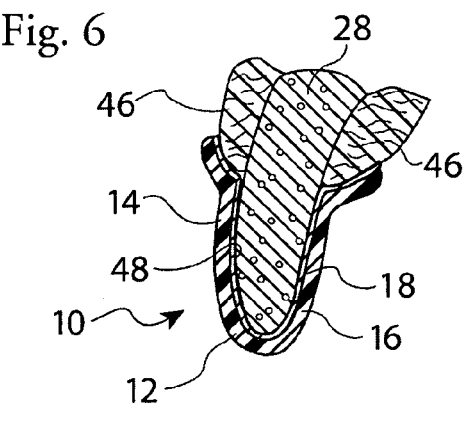
FIG. 6 is an enlarged scale sectional view, taken substantially along the plane 6—6 of FIG. 5 but with a coating of oral treatment preparation between the membrane and surfaces to be treated.

The lateral panel 16 is then bent around the occlusal surfaces of the teeth and manually manipulated in buccal and labial directions towards lingual and interdental tooth surfaces as well as adjacent gingival tissue until a corresponding inner face of the lateral panel 16 is shaped as illustrated in FIG. 5 and FIG. 6. It should be noted that in FIG. 6, the front panel 14 was modeled without the backing plate 20, so that its outer face is contoured around buccal tooth surfaces.

The applicator 10 may then be removed from the oral cavity, with the inner faces of the panels 14, 16 bearing impressions of tooth and gingival surfaces.

Thereafter, a layer or coating 48 of any of a number of available oral treatment preparations in paste, liquid or gel form or combinations thereof may be applied to the membrane 18 at the modeled impressions corresponding to the surfaces in need of treatment. Thus, if gingival tissue 46 or selected teeth or tooth surfaces are not in need of treatment, the preparation is not applied to the corresponding impression surfaces. The applicator 10 is then reinserted to administer the preparation.

Alternatively or conjunctively, a layer or coating 48 of preparation may be applied to the surfaces in need of treatment before the applicator is positioned for administration of the preparation.

The applicator is maintained in its administration position, e.g. as shown in FIG. 6, assuring intimate contact between the layer 48 of the treatment preparation and the target surfaces for a prescribed treatment duration. The fitted applicator 10 may be reused to administer oral treatment preparation in successive treatments.

Notably, the applicator 10 assures that the preparation will not inadvertently contact and possibly irritate non-target surfaces and also assures that the preparation itself will not be subject to dilution or diminution in effectiveness resulting from contact with saliva. Among the advantages of the applicator 10 is that during usage, it is relatively inconspicuous and does not impede speech.

The membrane 18 may constitute a smooth liquid impervious inert film surface and also serves to provide dimensional integrity and stability to the applicator core in areas, wherein the core 12 has been thinned during the fitting procedure. In some areas, the membrane may provide the sole supporting medium for carrying the coating 48 of oral treatment preparation.

It should be recognized that the membrane 18 may be precoated with the preparation, such as a gel, prior to fitting. In such instances, the applicator 10 is not removed after fitting and remains in place for one step fitting and administration of the preparation.

In FIG. 7 there is illustrated the alternate embodiment of the invention wherein like numerals have been employed to designate like components of the previous embodiment, however, bearing the suffix "a". An applicator 10a includes a core 12a having a vertical panel 14a and a lateral panel 16a substantially identical to the core 12 of the previous embodiment, however the core 12a is completely enveloped by a membrane 18a.

In FIG. 8 there is illustrated a further embodiment of the invention wherein like numerals have been employed to denote like components of the previous embodiments, however, bearing the suffix "b". An applicator 10b includes a core 12b having a vertical panel 14b and a lateral panel 16b encased in a membrane 18b substantially identical to the embodiment of FIG. 7, however a modified backing plate 20b is employed. The backing plate 20b includes a vertical wall 22b and a transverse horizontal ledge 24b, which underlies and supports a portion of lateral panel 16b.

In FIG. 9 there is illustrated another embodiment of the invention wherein like numerals have been employed to designate like components of the prior embodiments, however, bearing the suffix "c".

An applicator 10c includes a core 12c covered with a membrane 18c and preloaded, i.e. impregnated, with oral treatment preparation in either liquid, paste, gel or dry format, such that the applicator 10b remains in place after fitting, for one step fitting and administration.

The membrane 18c on the inner faces of a vertical panel 14c and a lateral panel 16c includes a plurality of perforations 54c and the core 12c includes a plurality of wells or pockets 56c which are open to the membrane 18c. Each well or pocket 56c carries a quantity 50c of oral treatment preparation which is extruded through the perforations.

Alternately, the wells or pockets 56c may carry microcapsules of treatment preparation or the microcapsules may be embedded throughout the core 14c. The microcapsules rupture, releasing the preparation through the perforations when the core 12c is deformed during modeling to receive tooth and gingival impressions. A further or alternate construction utilizes the perforations 54c to carry the preparation and/or the preparation is coated on the core or the core side of the membrane 18c and passes through the perforations 54c or as the result of permeability of the membrane 18c.

Figure 10:
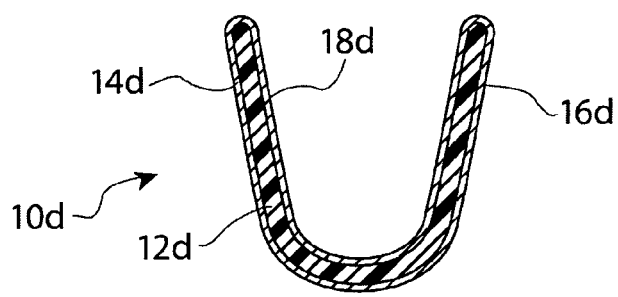
FIG. 10 is an enlarged scale sectional view similar to FIG. 2, but though a further embodiment wherein the applicator core is preformed prior to modeling impression of dentition surfaces.

With reference now to FIG. 10 where a still further embodiment of the invention is shown, an applicator 10d includes a core 12d covered with a membrane 18d. The core 12d comprises an arched shaped trough with a cross section similar to the letter "U" or "V" and includes a pair of opposed panels 14d, 16d joined together.

The core 12d may be formed of a rectangular sheet of modeling material having a longitudinal fold which separates the panels 14d, 16d. It is inserted into the oral cavity and positioned to overlay at least selected surfaces in need of treatment. Manual pressure is then applied, with the panel 14d being forced around buccal and interdental surfaces and the panel 16d being forced around lingual and interdental surfaces, to model the impression of such surfaces and thus assumes a shape substantially as shown in FIG. 5.

As previously mentioned, the applicator 10 is well suited for the topical administration of oral preparations formulated for various treatments such as tooth whitening, oral hygiene, prophylaxis, desensitization and palliation.

By way of example, suitable treatment preparations for tooth whitening applications include formulations, having as a constituent ingredient, one or more of the following: carbamide peroxide, urea peroxide, hydrogen peroxide, sodium perborate, sodium percarbonate, calcium hydroxide, magnesium carbonate, perhydrol urea and potassium chlorate.

Among the treatment preparations suitable for desensitization are formulations which include, as one or more constituent ingredients, benzalkonium chloride, potassium nitrate, citric acid, hydroxyethyl methacrylate, sodium fluoride, strontium chloride, butylated hydroxytpulene and citric acid salts.

Prophylaxis treatment preparations include formulations having constituent ingredients characterized by their ability to release fluoride ions in water, such as stannous fluoride, sodium fluoride, potassium fluoride, ammonium fluorosilicate, sodium monofluorophosphate, stannous chlorofluoride, tinfluoride and sodium fluorosilicate.

Pallative treatment preparations include formulations containing, as a constituent ingredient, one or more of the following, by way of example, eugenol, aloe, vitamin E and corticosteroid.

Topically applied preparations suitable for the alleviation of malodorous conditions include formulations containing, by way of example, carbamide peroxide and oxychlorine.

It should be understood that the foregoing examples are merely illustrative of the range of various oral treatment preparations which may be topically administered pursuant to the present invention.

Thus it will be seen that there is provided an oral applicator which achieves the various aspects, features and considerations of the present invention and which is well adapted to meet the conditions of practical usage.

Since various possible embodiments might be made of the present invention and since various changes might be made in the exemplary embodiments set forth herein without departing from the spirit of the invention, is to be understood that all matter herein described or shown in the accompanying drawings is to be interpreted as illustrative and not in a limiting sense.

Having thus described the invention, the following is claimed:

1. An applicator for topical administration of an oral treatment preparation, the applicator comprising an arch shaped pliable core, the core including a vertical first panel and a lateral panel, the core being formed of a modeling material capable of obtaining dental impressions by manual manipulation, a first face of the vertical panel and a first face of the lateral panel being covered with a plastic film membrane, the applicator further including an arch shaped removably positioned backing plate, the backing plate having a generally "L" shaped transverse section including a vertical wall abutting the vertical panel of the core and a horizontal ledge abutting at least a portion of the lateral panel whereby the first face of the vertical panel may be urged against buccal dentition surfaces to impress such surfaces in the vertical panel and the first face of the lateral panel may be bent against lingual dentition surfaces to impress such surfaces in the second panel so that an oral treatment preparation positioned between the core and one or more of the buccal and lingual surfaces is effectively administered.

2. An applicator for topical administration of an oral treatment preparation as constructed in accordance with claim 1 wherein the core is encased in the membrane.

3. An applicator for topical administration of an oral treatment preparation as constructed in accordance with claim 1 wherein the membrane is permeable.

4. An applicator for topical administration of an oral treatment preparation as constructed in accordance with claim 1 wherein the modeling material comprises wax.

5. An applicator for topical administration of an oral treatment preparation as constructed in accordance with claim 1 wherein the vertical panel includes impressions of buccal dentition surfaces and the lateral panel includes impressions of lingual dentition surfaces, the applicator further including a layer of oral treatment preparation.

6. An applicator for topical administration of an oral treatment preparation as constructed in accordance with claim 5, the oral treatment preparation being positioned over the membrane.

7. An applicator for topical administration of an oral treatment preparation as constructed in accordance with claim 1 wherein the core has a thickness in the range of approximately ½ mm to 3 mm.

8. An applicator for topical administration of an oral treatment preparation as constructed in accordance with claim 7 wherein the core has a substantially uniform thickness throughout.

9. A method of administering an oral treatment preparation, the method comprising the steps of:
   a) providing an applicator having a pliable core formed of modeling material, the core having a pair or panels and a plastic film overlay;
   b) providing the applicator with a removable barking plate having a generally "L" shaped transverse section including a vertical wall abutting one of the panels and a transverse ledge abutting at least a portion of the other panel;
   c) inserting the applicator core into an oral cavity;
   d) impressing buccal dentition surfaces in the one panel;
   e) impressing lingual dentition surfaces in the other panel; and
   f) positioning an oral treatment preparation between selected dentition surfaces and the impressions thereof formed in the panels.

10. A method of administering an oral treatment preparation in accordance with claim 9 wherein step f) is performed by:
   i) removing the applicator core from the oral cavity,
   ii) coating impressions of the core corresponding to the selected dentition surfaces with the oral treatment preparation, and
   iii) repositioning the core within the oral cavity.

11. A method of administering an oral treatment preparation in accordance with claim 9 wherein step f) is performed by:
   i) removing the applicator core from the oral cavity,
   ii) coating the selected dentition surfaces with the oral treatment preparation, and
   iii) repositioning the core within the oral cavity.

12. A method of administering an oral treatment preparation in accordance with claim 9 wherein step f) is performed by coating the selected dentition surfaces with the oral treatment preparation prior to step c).

13. An applicator for topical administration of an oral treatment preparation, the applicator comprising an arch shaped soft pliable core, the core including a vertical panel and a lateral panel and having a generally "L" shaped transverse section, the core being formed of a modeling material capable of obtaining dental impressions by manual manipulation, the applicator further including an arch shaped removably positioned backing plate, the backing plate having a generally "L" shaped transverse section including a vertical wall abutting the vertical panel of the core and a horizontal ledge abutting at least a portion of the lateral panel, whereby a first face of the vertical panel may be urged against buccal dentition surfaces to impress such surfaces in the vertical panel and the lateral panel may be bent around occlusal dentition surfaces and a fist face of the lateral panel may be urged against lingual dentition surfaces to impress such surfaces in the lateral panel so that an oral treatment preparation positioned between the core and one or more of the buccal, occlusal and lingual surface is effectively administered.

14. An applicator for topical administration of an oral treatment preparation as constructed in accordance with claim 13, wherein the first face of the vertical panel and the first face of the lateral panel are covered with a membrane.

15. An applicator for topical administration of an oral treatment preparation as constructed in accordance with claim 13, wherein the modeling material comprises wax.

16. A method of administering an oral preparation, the method comprising the steps of:
   a) providing an applicator having a carrier with a substantially "L" shaped transverse cross section throughout and a core with rheological characteristics suitable for implementation as a dental impression material,
   b) adhering a plastic film membrane over at least one face of the core,
   c) obtaining in the core impressions of buccal surfaces of selected target teeth by inserting the applicator in an oral cavity and applying lateral pressure against the carrier to force the core against the buccal surfaces of the selected target teeth, and
   d) positioning a layer of preparation between the buccal surfaces and the impressions formed in the core.

17. A method of administering an oral preparation in accordance with claim 16 wherein the preparation is carried in the core and the membrane is perforated, the step of positioning including:
   i) extruding the preparation through the perforations.

18. A method of administering an oral preparation in accordance with claim 16 wherein step d) is performed by:
   i) removing the applicator from the oral cavity,
   ii) coating the impressions of the buccal surfaces with the preparation, and
   iii) repositioning the core within the oral cavity.

19. A method of administering an oral preparation in accordance with claim 16 wherein step d) is performed by:
   i) removing the applicator from the oral cavity, ii) coating the buccal surfaces of the selected target teeth with the preparation, and
   iii) repositioning the core within the oral cavity.

* * * * *